United States Patent [19]
Meyer et al.

[11] Patent Number: 5,827,874
[45] Date of Patent: Oct. 27, 1998

[54] METHODS OF TREATING PAIN AND INFLAMMATION WITH PROLINE

[76] Inventors: Hans Meyer, Bäumliweg 18, 4125, Riehen; Segesser Bernhard, Gilgenbergstrasse 9, 4053, Basel, both of Switzerland

[21] Appl. No.: 638,765

[22] Filed: Apr. 29, 1996

[30] Foreign Application Priority Data

May 5, 1995 [CH] Switzerland .................. 01 301/95

[51] Int. Cl.$^6$ .................................................. A61K 31/40
[52] U.S. Cl. ................................................... 514/423
[58] Field of Search ............................................. 514/423

[56] References Cited

U.S. PATENT DOCUMENTS

| | | |
|---|---|---|
| 3,932,638 | 1/1976 | Coirre et al. . |
| 4,414,202 | 11/1983 | Silvetti . |
| 5,198,465 | 3/1993 | Dioguardi . |

FOREIGN PATENT DOCUMENTS

| | | |
|---|---|---|
| 0 324 227 | 7/1989 | European Pat. Off. . |
| 0 535 923 A1 | 4/1993 | European Pat. Off. . |
| 0 535 924 A1 | 4/1993 | European Pat. Off. . |
| 0 715 850 | 6/1996 | European Pat. Off. . |
| 174M | 6/1968 | France . |
| 24 38 703 | 3/1976 | Germany . |
| 25 07 223 | 9/1976 | Germany . |
| 25 47 243 | 4/1977 | Germany . |
| 35 38 619 | 5/1986 | Germany . |
| 56-133213 | 10/1981 | Japan . |
| 7-233147 | 9/1995 | Japan . |
| 7-267855 | 10/1995 | Japan . |
| 2171302 | 8/1986 | United Kingdom . |

OTHER PUBLICATIONS

Jemec and Moe, 1996, "Topical Treatment of Skin Ulcers in Prolidase Deficiency", Ped. Dermatol. 13:58–60.
Arata et al., 1986, "Effect of Topical Application of Glycine and Proline on Recalcitrant Leg Ulcers of Prolidase Deficiency", Arch. Dermatol. 122:626–627.
Meyers et al., 1979, "The Effect of Selected Amino Acids on Gelatin–Induced Inflammation in Adult Male Mice", Inflammation 3:225–233.
Chvapil, 1975, "Pharmacology of Fibrosis: Definitions, Limits and Perspectives", Life Sciences 16:1345–1361.
Geistlich, Chemical Abstracts, vol. 96, abstract No. 168773, Jan. 1982.
Lutostanska et al., 1993, "A Search for New Active Amino Acids Responsible for Pharmacological Activity of Collagen Degradation Products", Pol. J. Pharmacol. 45:253–268.
Budavari et al., 1989. *The Merck Index* (Merck & Co., Inc., Rahway, New Jersey) pp. 769, 1092, 1098, 1183–1184, 1236 and 1272–1273.
Sarhan and Seiler, 1989, "Proline and Proline Derivatives as Anticonvulsants", Gen. Pharmac. 20:53–60.
Negwer, 1987, *Organic–Chemical Drugs and their Synonyms* (Akademie–Verlag Berlin) pp. 49, 53 and 141.
Hayasaka et al., 1985, "Clinical Trials of Vitamin $B_8$ and Proline Supplementation for Gyrate Atrophy of the Choroid and Retina", Brit. J. Opthamol. 69:283–290.
Schubotz and Hausmann, 1977, "Treatment of Degenerative Arthropathies with N–Acetyl–Hydroxyproline", Therapiewoche 27:4248–4252.
Jacotot et al., 1971, "Prevention of Certain Acute and Chronic Effects of Nicotine by N–Acetyl–Hydroxyproline", Pathologie Biologie 19:497–502.
Huriez and Simon–Thery, 1971, "Action of a Derivative of Hydroxyproline—Specifically Contained in Collagen—in Cecatrization of Ulcers of the Legs", Lille Medical, 3me Serie 16:1197–1202.
Falbe and Regitz, *Rompp Chemie Lexikon*, 9. Ed. (Georg Thieme Verlag Stuttgart, New York) pp. 1908, 3627 and 3703, 1989.
Gerhartz et al., *Ullmann's Encyclopedia of Industrial Chemistry*, 5. Ed. (VCH Publishing) p. 86, 1989.

*Primary Examiner*—William R. A. Jarvis
*Attorney, Agent, or Firm*—Pennie & Edmonds LLP

[57] ABSTRACT

Methods of using proline for the treatment of inflammation and pain and especially for the treatment of inflammatory conditions, rheumatic and non-rheumatic pain and for post-operative or posttraumatic pain, are described.

7 Claims, No Drawings

METHODS OF TREATING PAIN AND INFLAMMATION WITH PROLINE

BRIEF SUMMARY OF THE INVENTION

The invention relates to the use of proline and/or 4-hydroxyproline as therapeutic agents, especially for the treatment for wounds as well as inflammation and/or pain. The invention also relates to pharmaceutical compositions comprising proline and/or 4-hydroxyproline and the preparation of such compositions.

BACKGROUND OF THE INVENTION

The L-form of proline (2-pyrrolidine-carboxylic acid) and 4-hydroxyproline (4-hydroxy-2-pyrrolidine-carboxylic acid) are naturally occurring amino acids and are found, for example, in great quantities in collagen. Elastin similarly contains proline in about each ninth residue: in contrast, it contains very little 4-hydroxyproline. Proline and 4-hydroxyproline are not considered to be essential amino acids.

Many N-substituted derivatives of proline or proline containing substituted peptides are known as ACE-inhibitors and became established for their ability to control highblood pressure (for example, Captopril, Moveltipril, Zofenopril, Lisinopril, Enalapril and Enalaprilat). Oxaceprol, an additionally N-acyl derivative, possesses antiphlogistic, antirheumatic and wound healing activity. Further, in EP-A-O 535 923 and EP-A-O 535 924, there are disclosed indole derivatives which can contain, in the one N-acyl amino acid residue, for example, a proline residue and this is disclosed to inhibit leukotriene-biosynthesis and possess antiasthmatic, antiallergic, antiphlogistic and cell-protective properties.

Commercial infusion solutions for parenteral nutrition occasionally contain proline as an adjunvant (for example, in combination with other amino acids, carbohydrates and electrolytes).

A clear pharmacological activity for non-derivatized proline and 4-hydroxyproline is not known and was medicinally, due to their abundant occurrence in nature, also not expected. Surprisingly, it has now been established by this invention that the referred to compounds possess significant antiphlogistic, antirheumatic, analgesic and wound healing promoting activity.

DETAILED DESCRIPTION OF THE INVENTION

The invention relates to proline and 4-hydroxyproline and their pharmaceutically acceptable salts for use as therapeutic agents, especially for use as antiphlogistic, antirheumatic or analgesic agents as promoters of wound healing, as well as pharmaceutical compositions for the treatment of inflammation or pain or for the treatment of wounds, particularly pharmaceutical compositions for the treatment of inflammatory conditions, rheumatic or non-rheumatic pain or for postoperative or posttraumatic pain. The pharmaceutical compositions of the invention comprises a therapeutically effective amount or quantity of proline and/or 4-hydroxyproline or a pharmaceutically acceptable salt thereof.

The invention further relates to the use of proline, and/or 4-hydroxyproline or a pharmaceutically acceptable salt thereof, to the preparation of pharmaceutical compositions and to a method for the treatment of inflammation or pain or for the treatment of wounds, especially a method for the treatment of inflammation, rheumatic or non-rheumatic pain or for postoperative or posttraumatic pain by the administration of a therapeutically effective amount of proline and/or 4-hydroxyproline or a pharmaceutically acceptable salt thereof.

In the scope of the present invention, proline shall preferably mean L-proline, and 4-hydroxyproline shall preferably mean 4-hydroxy-L-proline, particularly, trans-4-hydroxy-L-proline.

According to the invention, there come into consideration various forms of inflammatory conditions which cause pain, such as, rheumatic as well as non-rheumatic forms (and associated with existing motor barriers like, for example, epicondylitis) as well as postoperative or posttraumatic pain. While the mode of action is not now clear, inhibition of inflammation, inhibition and pain alleviation clinically show themselves with rheumatic illnesses and sport trauma in a clear improvement in the complaints of pain at rest, pain associated with movement, pain burden or load related, movement stiffness, swelling of ankles, as well in the increase in functionality.

In accordance with the invention, with respect to post-traumtic and postoperative inflammation and pain, the compositions of the invention cause a rapid reduction of spontaneous and motion caused pain and a reduction of inflammatory swelling and/or edema building. As selected examples of indications and therapies, in accordance with the invention, there come into consideration the following:

inflammatory and degenerative forms of rheumatism, chronic polyarthritis, juvenile chronic polyarthritis, ankylosing, spondylitis, arthrosis, and the like;

painful vertebral column;

rheumatism;

painful inflammation and swelling after injury and operations, for example, in orthopedics;

localized form of soft tissue rheumatism like, for example, tendovaginitis, shoulder-hand-syndrome, bursitis, and the like;

localized rheumatic diseases like, for example, arthrosis of peripheral joints and of the vertebral column, periarthritis, and the like;

traumatic and/or load related inflammation of tendons, torn ligaments, muscles and joints like, for example, spasms, bruises, pulling, and the like;

wound healing, and the like.

L-proline and 4-hydroxy-L-proline are naturally occurring substances and are present in nature in great quantities, their availability and supply is not a problem; toxic effects, such as, secondary effects and contraindications are, as yet, not known and also not expected. In comparison to the classic chemistry of analgesic and antiphlogistics, the substances comprising the invention allow for rapid, highly efficient and better therapy, without side effects and, therefore, also lead to improvement in patient compliance.

In accordance with the invention, the pharmaceutical compositions can contain proline, 4-hydroxyproline or a salt thereof alone or in combination and, as desired or appropriate, can also contain one or more additional active ingredients. Further, in the pharmaceutical compositions, in accordance with the invention, proline and/or 4-hydroxyproline can be present as such or in the form of a pharmaceutically acceptable salt, for example, in the form of the corresponding hydrochloride or sodium, calcium or magnesium salt. Especially valuable salts are those which contain, as acid components, vitamin acids, for examples, ascorbic acid, vitamin-A-acid and the like. The active ingredient content can vary in a broad range and, by way of exemplification, can be an amount in the range of from about 1 to 99 weight % of the particular pharmaceutical composition.

Proline, 4-hydroxyproline and their pharmaceutically acceptable salts are suited for use for the named indications or group of indications in all customary galenical forms. Such pharmaceutical administration forms comprise, for example, for gastric decomposition, tablets, dragees, capsules or the like, so called osmotic pump systems, one or more layered solid preparations from which one can choose a delayed or gradually releasing form, pellets in capsules or pressed with instantaneous or slower releasing materials, gastric juice resistant preparations encapsulating the active ingredients in soft gelatin capsules or sealing, by special methods, into hard gelatin capsules or other casings, forms that are soluble in water or other beverage, such as, for example, effervescent tablets, effervescent granules, soluble tablets and soluble granules, fluid preparations, such as, drops or syrups to be taken as concentrates or diluted in water or other beverages, transdermal forms for topical application, such as, plasters, gels, creams and similar fluid dosage forms for administration by injection or infusion, suppositories or other preparations for rectal administration. Preferred are solid or semisolid forms, such as, tablets, dragees, capsules, granulates, suppositories, gels, creams or salves, and liquid delivery systems, such as, solutions or suspensions.

The invention also relates to a process for the preparation of the pharmaceutical compositions of the invention, comprises bringing together a therapeutically effective amount of proline and/or 4-hydroxyproline or a pharmaceutically acceptable salt thereof, or mixtures thereof, with one or more therapeutically inert excipients in a galenical dosage form. For the preparation of a pharmaceutical composition, conventional procedures, for example, mixing, granulation, coating, dissolution, lyophilization, and the like can be utilized.

Pharmaceutical compositions for oral administration can, for example, include the steps of combining the active ingredient with a solid carrier, if necessary, granulating the resulting mixture, and processing the resulting mixture or granulate, if desirable or necessary, after the addition of a suitable adjuvant, into tablets or kernels for dragees.

Suitable carriers are: particularly fillers, such as, for example, lactose, saccharose, mannitol or sorbitol, cellulose and/or calcium phosphate, for example, tricalciumphosphate or calciumhydrogenphosphate; further, binding agents, such as, starch paste using, for example, corn, wheat, rice or potato starch, gelatin, tragacanth, methylcellulose, hydroxypropylmethylcellucose, sodium carboxymethylcellulose and/or polyvinylpyrrolidone; and/or when desirable, disintegrating agents, such as, the above mentioned starches, additionally, carboxymethylstarch, crosslinked polyvinylpyrrolidone, agar, allgin acid or a salt thereof, such as, sodium alginate. As adjuvants, suitable are, in the first instance, flow regulating and lubricating substances, for example, silicic acid, silicon dioxide, talc, stearic acid, or salts thereof, such as, magnesium or calcium stearate and/or polyethyleneglycol.

Additionally, suitable oral pharmaceutical dosage forms are one piece capsules made of gelatin, as soft one piece capsules of gelatin and a plasticizer, such as, glycerin or sorbitol. The one piece capsule can contain the active ingredient in the form of granules, for example, in a mixture of filler, such as lactose, binder, such as starch, and/or a lubricant, such as talc or magnesium stearate, and, if necessary, a stabilizer. In the soft capsule, the active ingredient is preferably dissolved or suspended in a suitable solvent, such as, a triglyceride, paraffin or liquid polyethyleneglycol, and also stabilizers can be added.

For parenteral administration, in the first instance, there comes into consideration: an aqueous solution of an active ingredient in water soluble form; further, suspensions of the active ingredients, such as, an injection suspension of the active ingredient in oily injection suspension, for which one can use or lypophyllic solvent or vehicle, such as, a triglyceride, for example, sesame oil, or a fatty acid ester, for example, ethlyloleate or triglyceride: or an aqueous injection suspension solution, which contains a viscosity increasing agent, for example, sodium carboxymethylcellulose, sorbitol and/or dextran and, if necessary, also a stabilizer.

Pharmaceutical compositions for topical use can be, for example, gels or hydrogels, creams and salves. The active ingredient(s) can be dissolved or suspended in the base at hand. In pharmaceutical usage, "Salve" is a customary notation for all applications comprising semi-soft preparation for use upon cutaneous membranes. In the following explanation, the name "Salve" will be used in the above ordered sense. Salves can be put together in a salve base, which can be, in a simple system, for example, vaseline or in a more complex system, for example, an emulsifiers based system, and an active ingredient or a combination of active ingredients.

Suitable salve bases contain, for example, vaseline, paraffin, polyethylene, natural hydrogenated or synthetic triglyceride, polyethyleneglycole, macrogoles, carbo waxes, cellulose and its derivatives, high dispersion silicon oxide, bentonite, starches, amylopectic and its derivatives, alginate, tragacanth, polyacrylic acid, polyvinyl alcohols and/or polyorylvinylpyrrolidone. Suitable emulsifiers are, for example, cetylstearylalcohol, cetylesteralcohol, sodium laurylsulfate, sodium cetylsulfate, sodium stearylsulfate, sorbitan ester, polysorbate, and polyoxyethyleneglyceride alcohol ether. Examples of suitable stabilizing agents are ethanol, isopropanol, sorbic acid, paraben (4-hydroxybenzoic acid), parabenester (4-hydroxybenzoic acid ester), methylparaben, propylparaben, hexachlorophen, benzalkonium bromide, cetylpyridinium chloride, and ascorbic acid. Suitable facilitators (also included are penetration enhancers, absorption accelerators and like) are, for example, isopropylmyristate, dimethylsulfoxide, 2-pyrrolidone, 1-dodecylazacycloheptan-2-one, 1,2-propyleneglycol, oleic acid, sodium laurylsulfate, urea, salicylic acid, hyaluronidase, oleyl alcohol, and ethyleneglycol.

The dosage regimen for the active ingredients utilized in the invention depends on the illness or condition to be treated, and is determined by the body weight and age of the patient, and the individual condition of the patient, as well as the applicable art and from the state of the best art. For oral and rectal administration, most suitable is, preferably, a dosage form containing with 50 to 5000 mg of proline and/or 4-hydroxyproline, respectively, a pharmaceutically acceptable salt thereof, per unit, taken 1 to 4 times a day. For topical application, suitable are semisolid or liquid preparations which contain 1 to 50% of proline and/or 4-hydroxyproline, respectively, a pharmaceutically acceptable salt thereof.

In two preliminary clinical investigations, two patient groups with chronic inflammations or trauma associated pain conditions were treated for five days with an oral, respectively, topical delivery system of a proline containing preparation. The first group received one tablet containing 500 mg of proline taken three times a day (product according to Example 1). The second group received a gel containing 5% by weight (product according to Example 2) which was applied to the painful spot or area two or three times a day. The patient were asked daily to give an evaluation of the intensity of the pain on a scale of 0 (no pain) to 9 (severe pain). The recorded absolute values (100% corresponds to the initial value on day 0) are disclosed together in Tables 1–4.

TABLE 1

Tablets containing 500 mg of Proline administered 3 times a day, recorded pain intensity on a scale of 0 to 9.

| Day | 0 | 1 | 2 | 3 | 4 | 5 |
| --- | --- | --- | --- | --- | --- | --- |
| Patient 1 Achillodynia | 7 | 7 | 7 | 6 | 4 | 3 |
| Patient 2 Myogelose + Muscle Pain Right Leg Bone | 7 | 7 | 8 | 7 | 5 | 5 |
| Patient 3 Tarsal Tunnel Syndrome | 9 | 9 | 9 | 5 | 4 | 5 |
| Patient 4 Aductor Connection Irritated Right Side | 3 | 3 | 2 | 1 | 1 | 1 |
| Patient 4 Achilles Tendon/ Soleus Irritation on Left Side | 2 | 2 | 1 | 0 | 0 | 0 |
| Patient 5 Compartment Syndrome | 4 | 4 | 4 | 4 | 3 | 2 |
| Average | 5.3 | 5.3 | 5.2 | 3.8 | 2.5 | 2.7 |

TABLE 2

Tablets containing 500 mg of Proline, administered 3 times a day. Normalized Pain Intensity in %

| Day | 0 | 1 | 2 | 3 | 4 | 5 |
| --- | --- | --- | --- | --- | --- | --- |
| Patient 1 Achillodynia | 100.0 | 100.0 | 100.0 | 85.7 | 57.1 | 42.9 |
| Patient 2 Myogelose + Muscle Pain Right Leg Bone | 100.0 | 100.0 | 114.3 | 100.0 | 71.4 | 71.4 |
| Patient 3 Tarsal Tunnel Syndrome | 100.0 | 100.0 | 100.0 | 55.6 | 44.4 | 55.6 |
| Patient 4 Aductor Connection Irritated | 100.0 | 100.0 | 66.7 | 33.3 | 33.3 | 33.3 |
| Patient 4 Achilles Tendon/Soleus Irritation on Left Side | 100.0 | 100.0 | 50.0 | 0 | 0 | 0 |
| Patient 5 Compartment Syndrome | 100.0 | 100.0 | 100.0 | 100.0 | 75.0 | 50.0 |
| Average | 100.0 | 100.0 | 88.5 | 62.4 | 46.9 | 42.2 |

TABLE 3

Gel Containing 5% by Weight of Proline, applied 2 to 3 times a day. Recorded Pain Intensity on a Scale of 0 to 9.

| Day | 0 | 1 | 2 | 3 | 4 | 5 |
| --- | --- | --- | --- | --- | --- | --- |
| Patient 1 Knee Pain | 5 | 5 | 3 | 3 | 4 | 2 |
| Patient 2 Achillodynia Right | 5 | 5 | 4 | 4 | 3 | 2 |
| Patient 2 Achillodynia Left | 5 | 5 | 4 | 4 | 3 | 2 |
| Patient 3 Achillodynia in the Morning | 7 | 7 | 6 | 3 | 1 | 3 |
| Patient 3 Achillodynia in the Evening | 5 | 5 | 3 | 1 | 2 | 2 |
| Patient 4 Elbow Dislocation | 4 | 4 | 3 | 2 | 1 | 2 |
| Patient 4 Cervical Vertebral Column Pain after an Accident | 6 | 4 | 3 | 2 | 1 | 1 |
| Patient 4 Shoulder Left | 7 | 7 | 8 | 7 | 4 | 3 |
| Patient 5 Bursitis Subachillea Right | 4 | 3 | 3 | 3 | 2 | 2 |
| Patient 6 Elbow Dislocation Left | 3 | 3 | 3 | 2 | 1 | 1 |
| Patient 7 Achillodynia | 4 | 4 | 5 | 3 | 3 | 2 |
| Average | 5.0 | 4.7 | 4.1 | 3.1 | 2.3 | 2.0 |

TABLE 4

Gel containing 5% by Weight of Proline, applied 2 to 3 times a day. Normalized Pain Intensity in %

| Day | 0 | 1 | 2 | 3 | 4 | 5 |
| --- | --- | --- | --- | --- | --- | --- |
| Patient 1 Knee Pain | 100.0 | 100.0 | 60.0 | 60.0 | 80.0 | 40.0 |
| Patient 2 Achillodynia Right | 100.0 | 100.0 | 80.0 | 80.0 | 60.0 | 40.0 |
| Patient 2 Achillodynia Left | 100.0 | 100.0 | 80.0 | 80.0 | 60.0 | 40.0 |
| Patient 3 Achillodynia in the Morning | 100.0 | 100.0 | 85.7 | 42.9 | 14.3 | 42.9 |
| Patient 3 Achillodynia in the Evening | 100.0 | 100.0 | 60.0 | 20.0 | 40.0 | 40.0 |
| Patient 4 Elbow Dislocation Right | 100.0 | 100.0 | 75.0 | 50.0 | 25.0 | 50.0 |
| Patient 4 Cerival Vertebral Column Pain after an Accident | 100.0 | 66.7 | 50.0 | 33.3 | 16.7 | 16.7 |
| Patient 4 Shoulder Left | 100.0 | 100.0 | 114.3 | 100.0 | 57.1 | 42.9 |
| Patient 5 Bursitis Subachillea Right | 100.0 | 75.0 | 75.0 | 75.0 | 50.0 | 50.0 |
| Patient 6 Elbow Dislocation Left | 100.0 | 100.0 | 100.0 | 66.7 | 33.3 | 33.3 |
| Patient 7 Achillodynia | 100.0 | 100.0 | 125.0 | 75.0 | 75.0 | 50.0 |
| Average | 100.0 | 94.7 | 82.3 | 62.1 | 46.5 | 40.5 |

As the results of the investigation show, the effects of both pharmaceutical formulations is a surprising fast decrease of chronic pain.

The foregoing invention is further illustrated by the examples which follow. As used herein, Avicel PH 102 (microcrystalline Cellulose; FMC Corp.), Explotab (Sodium starchglycolate; Mendell, Patterson, N.Y.), Syloid 244 (Silica gel; W.R. Grace/Davison Div., Baltimore), Cutins HR (Wax mixture, ethyloxylated Ester; Henkel), Polysorbate 80 (Polyoxyethylenesorbitan ester; ICI), Carbopol 980 (Polyacrylic acid; BFGoodrich), PVP K30 (Polyvinylpyrrolidone, also known as, Polyvidon; GAF, England), Eudragit (Acryl resin; Rohm, Germany) and Natrosol 250 HX (Hydroxyethylcellulose; Aqualon, Germany) are known commercial products. Temperature are given in Celsius degrees.

EXAMPLE 1

PREPARATION OF TABLETS

Tablets containing 500 mg of proline can be prepared as follows (formulation for 1 and 1000 tablets):

|  | mg/Tablet | g/1000 Tablets |
|---|---|---|
| Proline | 500.0 | 500.0 |
| Avicel PH 102 | 86.0 | 86.0 |
| Explotab | 50.6 | 50.6 |
| Syloid 244 | 3.2 | 3.2 |
| Cutina HR | 5.2 | 5.2 |

Proline, Avicel and Explotab are mixed together homogenously for 10 minutes.

Thereafter, Syloid and Cutina are mixed in for one minute. The finished mixture is compressed into tablets (Weighing 645 mg each).

EXAMPLE 2

PREPARATION OF A GEL

A gel containing 5% of proline or hydroxyproline, as the active ingredient, can be prepared as follows (formulation of 1 kg of gel):

|  | g/kg Gel |
|---|---|
| Active Ingredient | 50.0 |
| Isopropylmyristate | 20.0 |
| Polysorbate 80 | 60.0 |
| Carbopol 980 | 8.0 |
| Isopropanol | 380.0 |
| Water | 442.0 |
| NaOH 1N | 40.0 |

Partial Product 1

Isopropylmyristate and Polysorbate 80 are mixed together homogeneously. Then, isopropanol is mixed in. When the mixture is homogeneous, Carbopol is slowly added with stirring and, thereafter, heated for 10 minutes.

Partial Product 2

The active ingredient is added to the water and heated for so long as it takes to completely dissolve it.

Finished Gel Product

With stirring, partial product 1 and 2 are mixed together and the mixture is heated further for 10 minutes. The vessel containing the mixture is covered and allowed to stand overnight. The next day the mixture is heated for 10 minutes, then, while stirring, it is treated with a thin stream of 1N NaOH (the pH of the gel should be between 6 and 7) and heated for an additional 15 minutes. The gel is collected or filled into a suitable topical dosage unit, for example, aluminium or plastic tubes.

EXAMPLE 3

DELAYED OR SLOW RELEASE TABLETS

Such tablets, containing 200 mg of proline, can be prepared as follows (Formulation for 1 and 1000 such tablets):

|  | mg/Tablet | g/1000 Tablets |
|---|---|---|
| Proline | 200 | 200 |
| PBP K30 | 125 | 125 |
| CaHPO$_4$ | 25 | 25 |
| Eudragit RS | 131 | 131 |
| Natrosol 250 HX | 100 | 100 |

To prepare a granulation solution for 1000 Slow Release Tablets, 92 g of isopropanol and 62 g of acetone are added together and mixed with stirring. Thereafter, 6 g of Eudragit RS are interspersed with stirring, and is heated further, until all are dissolved.

To prepare a granulation of the active ingredient to produce 1000 Slow Release Tablets, 200 g of proline, 125 g of PVP K30, 25 g of calciumhydrogenphosphate, 125 g of Eudragit RS and 100 g of Natrosol 250 HS are homogeneously mixed together for 5 minutes. The pulverized mixture is passed through a 0.7 mm sieve and again homogenized in a mixer over a 5 minute period. Thereafter, the pulverized mixture is moistened with the granulation solution and homogeneously mixed. The resulting mixtures again passed through a 0.7 mm sieve and dried at 45 degrees. The resulting dried mixture is once more passed through the 0.7 mm sieve. The resulting mixture is pressed into Slow Release Tablets (weighing 581 mg).

We claim:

1. A method of treating inflammation, or pain which comprises administering to an animal requiring such treatment a pharmaceutical composition comprising a therapeutically effective amount of proline, as the active ingredient or a pharmaceutically acceptable salt thereof or mixtures thereof.

2. The method of treating inflammation or pain of claim 1, which comprises administering a semi liquid, solid or liquid pharmaceutical dosage form.

3. The method of claim 2, wherein the therapeutically effective amount of L-proline is in the range of 50 mg to 5000 mg.

4. The method of claim 2, wherein the therapeutically effective amount of L-proline is in the range of from about 1% to about 50%.

5. The method of claim 3 or 4, wherein the salt is proline ascorbate.

6. The method of claim 1, wherein the animal is a human.

7. The method of claim 1, wherein the pain is rheumatic, nonrheumatic, or postoperative posttraumatic pain.

* * * * *